(12) United States Patent
Gautschi et al.

(10) Patent No.: US 6,492,563 B2
(45) Date of Patent: Dec. 10, 2002

(54) FRAGRANCE PRECURSORS

(75) Inventors: Markus Gautschi, Zeiningen (CH); Caroline Plessis, Yvre le Polin (FR); Samuel Derrer, Fallanden (CH)

(73) Assignee: Givaudan SA, Dubendorf (CH)

( * ) Notice: Subject to any disclaimer, the term of this patent is extended or adjusted under 35 U.S.C. 154(b) by 0 days.

(21) Appl. No.: 09/829,777

(22) Filed: Apr. 10, 2001

(65) Prior Publication Data

US 2002/0077508 A1 Jun. 20, 2002

(30) Foreign Application Priority Data

Apr. 10, 2000 (EP) .............................. 00107680

(51) Int. Cl.$^7$ ..................... C07C 49/115; C07C 49/215; C07C 49/782

(52) U.S. Cl. ................ 568/327; 568/328; 568/329; 568/331; 568/337; 568/376; 568/377

(58) Field of Search ............... 568/327, 328, 568/329, 331, 337, 376, 377

(56) References Cited

U.S. PATENT DOCUMENTS 6,222,062 B1 * 4/2001 Anderson et al.
6,258,854 B1 * 7/2001 Anderson et al.

FOREIGN PATENT DOCUMENTS

EP 936 211 A3 8/1999
WO WO 99/60990 12/1999

OTHER PUBLICATIONS

Arimoto et al., 1998, "Synthesis and Absolute Stereochemistry of Tanzawaic acid (GS–1302)", Tetrahedron Lett. 39(51): 9513–9516.
Honda et al., 1987, "A General Synthetic Method Of Chiral 2–Arylalkanoic Esters Via Thermal 1,2–Rearrangement", Bull. Chem. Soc. Japan, 60(3): 1027–36.
McGarvey, et al., 1985, "A Trialkylstannane–Mediated Approach To Acyloin Products", J. Org. Chem., 50(23): 4655–7.
Umezawa et al., 1984, "Incorporation of H$_2$ $^{18}$O into the C$_\alpha$ but not the C$_\beta$ Position in the Degradation of a β O–4 Lignin Substructure Model by *Phanerochaete chrysosporium*", Agric. Biol. Chem., 48–(7):1917–21.
Zhu et al., (1998), "Practical Syntheses of β–Amino Alcohols via Asymmetric Catalytic Hydrogenation", J. Org. Chem., 63(23):8100–8101.
Copy of European Patent Office Communication dated Jan. 21, 2002 transmitting a European Search Report for EP Patent No. 01106425.0–2103.
Crich, et al., *Tetrahedron*, 51, 11945–11952 (1995). "Intramolecular Hydrogen Atom Abstraction".
R.M. Cowper, et al., *Org. Synth. Coll.*, vol. 2:480–81 (1943), "Phenacyl Biomide".

* cited by examiner

Primary Examiner—James O. Wilson
Assistant Examiner—Sikarl A. Witherspoon
(74) Attorney, Agent, or Firm—Fish & Richardson PC

(57) ABSTRACT

The present invention is a fragrance precursor of formula I:

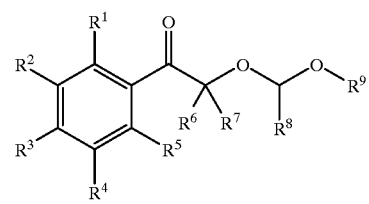

(I)

Figure 1:
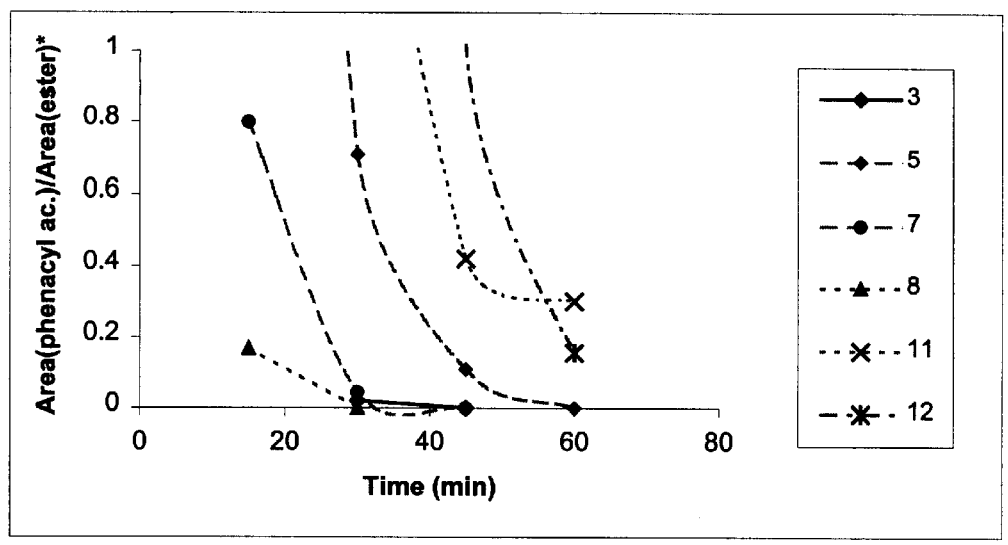

for a fragrant ketone of formula II:

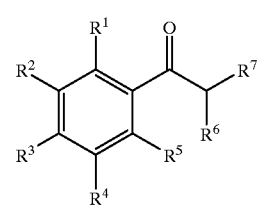

(II)

and a fragrant ester of formula III:

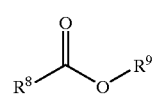

(III)

wherein,
$R^1$ to $R^5$ represent independently H, —NO$_2$, linear or branched C$_1$–C$_6$-alkyl, C$_1$–C$_6$-alkenyl, C$_1$–C$_6$-alkinyl or C$_1$–C$_4$-alkoxy,
$R^1$ and $R^2$, $R^2$ and $R^3$, $R^3$ and $R^4$, and $R^4$ and $R^5$ may form together one or two aliphatic or aromatic rings,
$R^6$ and $R^7$ are independently H, linear or branched C$_1$–C$_6$-alkyl-, C$_1$–C$_6$-alkenyl, C$_1$–C$_6$-alkinyl, and
$R^8$ and $R^9$ are the residues of an acid $R^8$-COOH and an alcohol $R^9$OH respectively forming the fragrant ester of formula III. A method for providing an odor by admixing with a product a fragrance precursor as detailed above.

24 Claims, 1 Drawing Sheet

FRAGRANCE PRECURSORS

FIELD OF THE INVENTION

The present invention relates to fragrance precursors for a fragrant ketone and a fragrant ester. Compositions containing such fragrant precursors are also provided. A process for imparting a fragrance to a substrate using such a fragrance precursor is also provided.

BACKGROUND OF THE INVENTION

A principal strategy currently employed in imparting odors to consumer products is the admixing of the fragrance directly into the product. There are, however, several drawbacks to this strategy. The fragrance material can be too volatile and/or too soluble, resulting in fragrance loss during manufacturing, storage, and use. Many fragrance materials are also unstable over time. This again results in loss during storage.

In many consumer products it is desirable for the fragrance to be released slowly over time. Microencapsulation and inclusion complexes with cyclodextrins have been used to help decrease volatility, improve stability and provide slow-release properties. However, these methods are, for a number of reasons, often not successful. In addition, cyclodextrins can be too expensive.

Precursors for the delivery of organoleptic compounds, especially for flavors, fragrances and masking agents are described in EP-A 0 936 211. This delivery system releases one or more odoriferous compounds upon exposure to light and/or UV irradiation. Using this system in various consumer products leads to a prolonged perception of the fragrant compound(s) to be released.

WO 99/60990 describes fragrance precursors which release fragrant alcohols, aldehydes or ketones upon exposure to light. Perfuming compositions containing these fragrance precursors can be used in various consumer products such as detergents, fabric softeners, household products, hair care products, etc.

It is known that phenacyl glycosides undergo a Norrish Type II photoreaction leading to gluconolactones and the corresponding phenacyl compound (Crich et al., Tetrahedron, 1995, 51, 11945–11952). However, it has not been described or suggested to use such phenacyl acetals as fragrance precursors, which are capable of releasing a fragrant ketone and a fragrant ester over a prolonged period.

Many fragrant compounds with odors accepted by the public are esters of high volatility resulting in a short period of perceivable odor. Such esters are quickly hydrolyzed in an alkaline environment, thereby losing the fragrant characteristic. Therefore, they are of limited use for laundry products.

SUMMARY OF THE INVENTION

It is therefore desirable to have a fragrance delivery system which is capable of releasing the fragrant compound or compounds in a controlled manner, while maintaining a desired odor over a prolonged period of time.

An object of the present invention is to provide non-volatile precursors for volatile fragrant esters.

Another object of the present invention is to provide fragrance precursors which are stable in an alkaline environment, especially in laundry products.

A further object of the present invention is to provide fragrance precursors with high substantivity.

Another object of the present invention is to provide fragrance precursors which are activated and cleaved by light.

A further object of the present invention is to provide fragrance precursors with slow release properties.

Accordingly, one embodiment of the invention is a fragrance precursor of formula I:

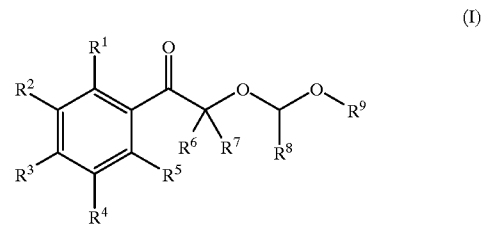

(I)

for a fragrant ketone of formula II:

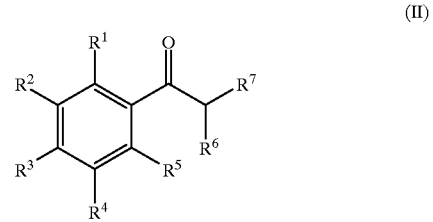

(II)

and a fragrant ester of formula III:

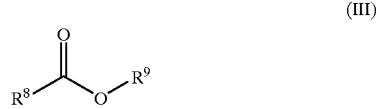

(III)

wherein, $R^1$ to $R^5$ represent independently H, $-NO_2$, linear or branched $C_1-C_6$-alkyl, $C_1-C_6$-alkenyl, $C_1-C_6$-alkinyl, or $C_1-C_4$-alkoxy, $R^6$ and $R^7$ are independently H, linear or branched $C_1-C_6$-alkyl-, $C_1-C_6$-alkenyl, or $C_1-C_6$-alkinyl, $R^8$ and $R^9$ are the residues of an acid $R^8$-COOH and an alcohol $R^9$OH respectively forming the fragrant ester of formula III.

Another embodiment of the invention is a composition containing a base and a fragrance precursor of formula I:

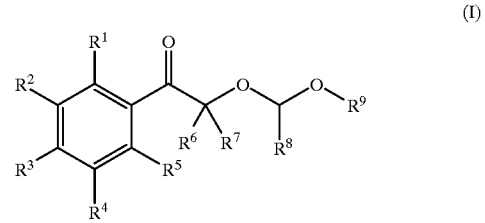

(I)

that upon exposure to light forms a fragrant ketone of formula II:

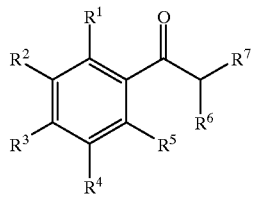

and a fragrant ester of formula III:

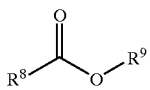

wherein,

R$^1$ to R$^5$ represent independently H, —NO$_2$, linear or branched C$_1$–C$_6$-alkyl, C$_1$–C$_6$-alkenyl, C$_1$–C$_6$-alkinyl or C$_1$–C$_4$-alkoxy, R$^1$ and R$^2$, R$^2$ and R$^3$, R$^3$ and R$^4$, and R$^4$ and R$^5$ may form together one or two aliphatic or aromatic rings, R$^6$ and R$^7$ are independently H, linear or branched C$_1$–C$_6$-alkyl-, C$_1$–C$_6$-alkenyl, C$_1$–C$_6$-alkinyl, and R$^8$ and R$^9$ are the residues of an acid R$^8$-COOH and an alcohol R$^9$OH respectively forming the fragrant ester of formula III.

A further embodiment of the invention is a process for providing a fragrance to a substrate having the steps of:

(a) contacting a substrate with a composition comprising fragrance precursor of formula I:

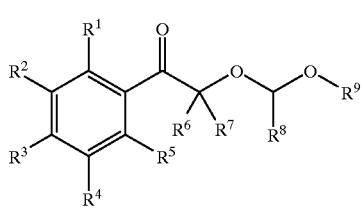

wherein,

R$^1$ to R$^5$ represent independently H, —NO$_2$, linear or branched C$_1$–C$_6$-alkyl, C$_1$–C$_6$-alkenyl, C$_1$–C$_6$-alkinyl or C$_1$–C$_4$-alkoxy, R$^1$ and R$^2$, R$^2$ and R$^3$, R$^3$ and R$^4$, and R$^4$ and R$^5$ may form together one or two aliphatic or aromatic rings, R$^6$ and R$^7$ are independently H, linear or branched C$_1$–C$_6$-alkyl-, C$_1$–C$_6$-alkenyl, C$_1$–C$_6$-alkinyl, and R$^8$ and R$^9$ are the residues of an acid R$^8$—COOH and an alcohol R$^9$OH respectively forming the fragrant ester of formula III; and (b) exposing the substrate to light source, to form a fragrant ketone of formula II:

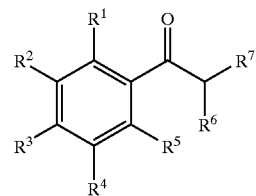

and a fragrant ester of formula III:

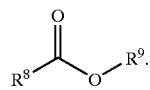

DETAILED DESCRIPTION OF THE INVENTION

The present invention relates to fragrance precursors of formula I:

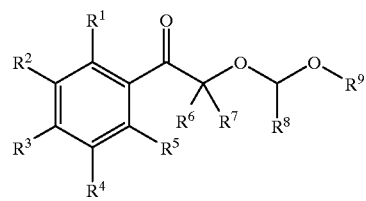

which upon exposure to light, and in particular daylight, release a fragrant ketone of formula II:

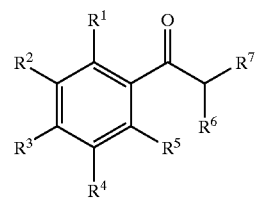

and a fragrant ester of formula III:

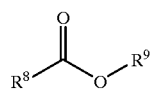

wherein

R$^1$ to R$^5$ represent independently H, —NO$_2$, branched or linear C$_1$-C$_6$-alkyl, C$_1$-C$_6$-alkenyl, C$_1$–C$_6$-alkinyl, or C$_1$–C$_4$-alkoxy, R$^1$ and R$^2$, R$^2$ and R$^3$, R$^3$ and R$^4$, and R$^4$ and R$^5$ may form together one or two aliphatic or aromatic rings, these rings may optionally contain branched or linear C$_1$–C$_4$-alkyl, C$_1$–C$_4$-alkenyl, or C$_1$–C$_4$-alkinyl residues, and the above rings and residues may contain one or more oxygen atoms, R$^6$ and R$^7$ are independently H, branched or linear C$_1$–C$_6$-alkyl, C$_1$–C$_6$-alkenyl, or C$_1$–C$_6$-alkinyl, and R$^6$ or R$^7$ may form with either $R^1$ or $R^5$ a carbocyclic ring optionally substituted by an aliphatic residue.

Scheme A

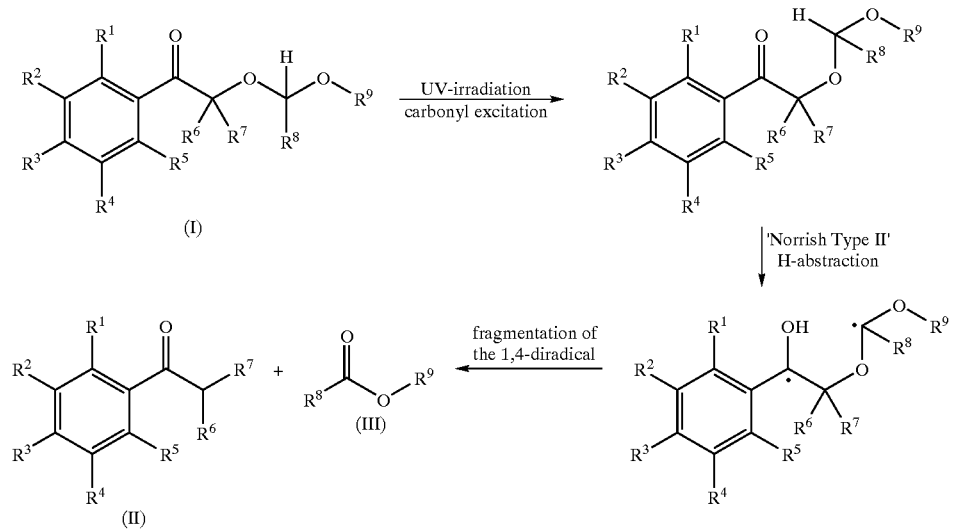

$R^8$ and $R^9$ are the residues of an acid $R^8$—COOH and an alcohol $R^9$OH respectively forming the fragrant ester of formula III.

The branched carbon chains defined above also may have multiple branched chains.

The fragrance precursors of formula I release, upon exposure to light, volatile fragrant esters of formula III and fragrant ketones of formula II. Because the precursors of the invention are stable in an alkaline environment, and show high substantivity, they are well adapted for detergent and laundry use.

The fragrance precursors of the present invention are slowly cleaved when exposed to light, in particular daylight. Upon absorption of energy from the light, the phenacyl acetals of formula I undergo a Norrish Type II photoreaction, which leads to the release of a fragrant ketone of formula II and a fragrant ester of formula III.

The release of the above mentioned fragrant compounds occurs, for example, upon exposure to a UV radiation source, such as sunlight penetrating through ordinary windows, although the light need not be particularly rich in UV irradiation. Upon exposure to bright sunlight, in particular direct sunlight from the outdoors, the release of the fragrant compounds of formula II and III will occur faster and to a greater extent than upon exposure to room light inside a building. The cleavage of the precursors of the present invention can also be initiated by an appropriate lamp, for example, a sun tanning lamp.

The photoreaction of the fragrance precursors of formula I involves, in a first step, the absorption of light by the keto-group followed by abstraction of the acetal-H atom and subsequent cleavage of the resulting 1,4-diradical (Scheme A). It has been found that the aromatic residue of the fragrance precursors plays an important role in this photoreaction as it influences the absorption maxium $\lambda_{max}$ of the keto-group. Therefore, the cleavage properties of the fragrance precursors can be modified by variation of the substituents $R^1$ to $R^5$.

The fragrant ketones of formula II may be used as an ingredient for the formulation of perfumes or perfumed articles using well known techniques. Non-limiting examples of aryl alkyl ketones of formula I include acetanisole (1-(4-methoxyphenyl)-ethanone) (Givaudan Roure (International) SA, Vernier, Switzerland), acetophenone (1-phenyl-ethanone) (Haarmann & Reimer GmbH, Germany), Crysolide® (4-acetyl-6-tert-butyl-1,1-dimethyl-indan) (Givaudan Roure (International) SA, Vernier, Switzerland), dimethyl acetophenone (1-(2,4-dimethylphenyl)-ethanone) (Fluka AG, Buchs, Switzerland), Fixolide® (1-(5,6,7,8-tetrahydro-3,5,5,6,8,8-hexamethyl-2-naphthalenyl-ethanone) (Givaudan Roure (International) SA, Vernier, Switzerland), Florantone T® (1-(5,6,7,8-tetrahydro-2-naphthalenyl)-ethanone) (Takasago Perfumery Co., Japan), Grassenone 34® (3-methyl-1-(4-methylphenyl)-4-hexen-1-one) (Keemia Institute, Tallin USSR), isopropylindanone (2-(1-methylethyl)-indanone) (Givaudan Roure (International) SA, Vernier, Switzerland), Lavonax® (1-phenyl-4-penten-1-one) (International Flavors & Fragrances, USA), Musk F (5-acetyl-1,1,2,3,3-pentamethyl-indane) (CNNP), Musk ketone® (4-tert-butyl-3,5-dinitro-2,6-dimethyl-acetophenone) (Givaudan Roure (International) SA, Vernier, Switzerland), Novalide® (1,6,7,8-tetrahydro-1,4,6,6,8,8-hexamethyl-indacen-3(2H)-one) (Givaudan Roure (International) SA, Vernier, Switzerland), Oranger Crystals® (1-(2-naphthalenyl)-ethanone) (Givaudan Roure (International) SA, Vernier, Switzerland), Orinox® (1-[4-(1,1-dimethylethyl)-2,6-dimethylphenyl]-ethanone) (Polak's Frutal Works BV, Netherlands), Phantolide® (1-(2,3-dihydro-1,1,2,3,3,6-hexamethyl-1H-inden-5-yl-ethanone) (Polak's Frutal Works BV, Netherlands), propiophenone (1-phenyl-propanone) (Haarmann & Reimer GmbH, Germany), Traseolide 100® (1-[2,3-dihydro- 1,1,2,6-tetramethyl-3-(1-methylethyl-1H-inden-5-yl-ethanone) (Quest International, Netherlands), Vernolide® (1-(5,6,7,8- tetrahydro-3', 5', 5', 8', 8'-penta-methyl-2-naphthalenyl)-ethanone) (Givaudan Roure (International) SA, Vernier, Switzerland), Versalide® (1-(5,6,7,8-tetrahydro-3'-ethyl,5', 5', 8', 8'-tetramethyl-2-naphthalenyl)-ethanone) (Givaudan Roure (International) SA, Vernier, Switzerland), and Vitalide® (1-(hexahydrodimethyl-1H-benzindenyl)-ethanone) (Takasago Perfumery, Japan).

The above list is illustrative only and is not intended to limit fragrant ketones of formula II. For example, additional fragrant ketones of formula II are e.g., described in "Perfume and Flavor Chemicals," S. Arctander Ed., Vol. I & II, Allured Publishing Corporation, Carol Stream, USA, 1994 and in K. Bauer, D. Garbe and H. Surburg, Eds., Common Fragrance and Flavor Materials, Wiley-VCH, $3^{rd}$ Edition, Weinheim, 1997.

Fragrance esters of formula III represent an important class of perfumery raw materials and include compounds of a great structural variety. Fragrance esters of formula III contribute to the odor and aroma of nearly all fruits and are known to be useful ingredients for the formulation of perfumes or perfumed articles. In the following, a non-limiting list of such esters are given as examples.

Most of the aliphatic esters of formula III are either acetates or include ethanol as the alcohol component. Examples of such esters of formula III include amyl butyrate, butyl 2-methylpentanoate, 3,7-dimethyloctan-3-yl acetate, ethyl 2-methylbutyrate, hexyl acetate, hexyl isobutyrate, and isopropyl 2-methylbutyrate.

The lower fatty acid esters of acyclic terpene alcohols, e.g. geraniol, linalool, and citronellol, and of cyclic terpene alcohols, e.g. menthol, α-terpineol, borneol, and guaiyol, are important both as fragrance and as flavor substances, and are envisaged as esters of formula III.

Various cycloaliphatic esters of formula III are widely used as perfumery chemicals, and include, for example: Agrumex® (2-tert-butylcyclohexyl acetate) (Haarmann & Reimer GmbH, Germany), Vertenex® (4-tert-butylcyclohexyl acetate) (International Flavors & Fragrances, USA), Verdylacetate® (4,7-Methano-3a,4,5,6,7,7a-hexahydro-5(6)-indenyl acetate) (Givaudan Roure (International) SA, Vernier, Switzerland), Givescone® (ethyl 2-ethyl-6,6-dimethyl-2-cyclohexenecarboxylate and ethyl 2,3,6,6-tetramethyl-2-cyclohexenecarboxylate) (Givaudan Roure (International) SA, Vernier, Switzerland), Cyclogalbanat® (allyl cyclohexyloxyacetate) (DRAGOCO Gerberding & Co. AG, Germany), Methyl jasmonate® (3-oxo-2-(cis-pentenyl)cyclo-pentaneacetic acid methyl ester) (Firmenich S.A., Switzerland), and Hedion® (methyl (3-oxo-2-pentyl-cyclopentyl)acetate) (Firmenich S.A., Switzerland).

Other important esters of formula III used in perfumery are those derived from araliphatic alcohols and aliphatic acids. Such compounds have characteristic odor properties. Important esters that fall into this category are e.g. benzyl acetate, phenethyl acetate, α,α-dimethylphenethyl acetate, and cinnamyl acetate.

Many of the esters of formula III described above, which are of pleasant odor, have a rather high volatility. This is especially true for aliphatic esters exhibiting typical fruity odors and for lower fatty acid esters of acyclic terpene alcohols having pleasant, citrusy, floral odors. An example of such a volatile ester is e.g. cis-3-hexenyl acetate. Cis-3-hexenyl acetate when applied to a surface of a substrate, for example, a fabric using a fabric softener in the rinsing cycle of the washing process, can only be perceived over a short period of time of one or two hours, depending on the concentration of cis-3-hexenyl acetate in the fabric softener.

The fragrance precursors of the present invention are not, or only slightly, volatile. The fragrant ketone of formula II and the fragrant ester of formula III are released only upon exposure to light, especially daylight. The photochemical cleavage provides over days and weeks perceptible amounts of the fragrant compounds. The period of release depends inter alia on the amount or concentration of the precursor applied to a substrate, the duration of exposure to light, its intensity, and its wavelength.

Fragrance esters of formula III are prone to undergo hydrolysis into an acid of formula $R^8COOH$ and an alcohol of formula $R^9OH$, especially in alkaline products. Therefore, many fragrance accords containing such esters, e.g. fruity accords, cannot be imparted to such products.

Today's consumers select a certain product not only based on performance but also based on the odor. From the foregoing it is evident that products for introducing a variety of fragrance accords to products having alkaline pH are desirable. The fragrance precursors of the present invention have the advantage that they are not or only slightly volatile and are chemically stable in consumer products having alkaline and neutral pH. A precursor of formula I added to, e.g., a powder detergent is stable in the detergent powder throughout storage. During the washing cycle (alkaline pH) and the rinsing cycle (neutral pH), the precursor is deposited on the fabric surface. It is only upon exposure of the fabric to light, for example during line drying in the sun, that the release of the fragrant ketone of formula II and the fragrant ester of formula III is started.

It has been noted above that esters of formula III, and especially the aliphatic ones, are rather volatile compounds. Furthermore, they are water soluble and are, therefore, lost to some extent during the washing/rinsing cycle, if introduced directly into detergents.

The fragrance precursors of formula I have the advantage that they have good substantivity on different substrates, especially on fabrics. Furthermore, the precursors are not or only slightly volatile, thus no loss occurs during storage. With the precursors of the present invention, highly volatile esters of formula III with low substantivity are successfully applied to achieve a long lasting pleasant odor. The volatile esters are produced in situ after application of the precursors of formula I onto a fabric during the washing cycle.

In the precursors of the invention, the moiety derived from a fragrant ketone of formula II brings three advantages: it introduces stability and substantivity to the precursors of formula I, and upon activation by light exhibits fragrant properties.

The fragrance precursors of the present invention are advantageously prepared via two methods. Both methods use an α-hydroxy-ketone as starting material. The latter is prepared by bromination of the corresponding fragrant ketone followed by sodium formate treatment and subsequent hydrolysis as shown in scheme I:

Scheme I

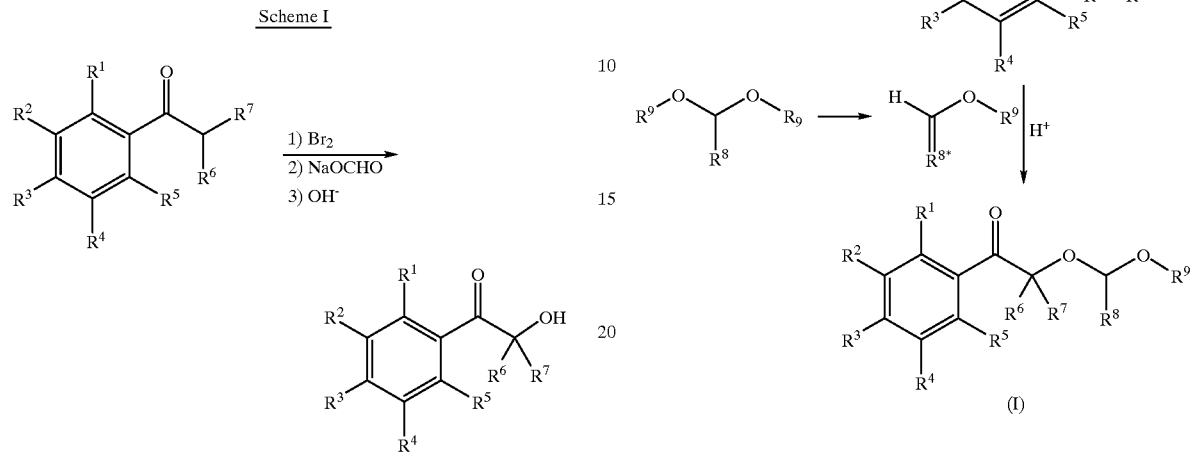

According to the first method, the α-hydroxy-ketone intermediate is reacted under acid conditions with a vinyl ether to the desired precursor of formula I. The vinyl ether is obtained via the acetal of an aldehyde $R^8CHO$ and an alcohol $R^9OH$. The synthesis is illustrated in scheme II:

Scheme II

According to the second method, the α-hydroxy-ketone is transformed to the corresponding vinyl ether using a Hg catalyst. The vinyl ether is then coupled with the alcohol $R^9OH$ from which the fragrant ester of formula III is derived. This method allows for the use of a great variety of alcohols, i.e. residues $R^9$ especially for allylic residues. The synthesis via this route is illustrated in scheme III:

Scheme III

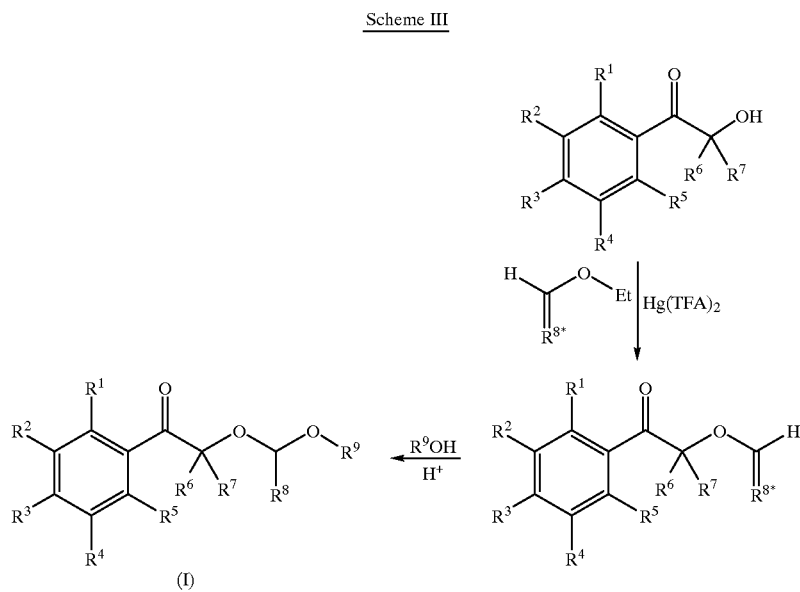

Preferred precursors of the present invention are compounds releasing an aliphatic ester of formula III wherein $R^8$ is the residue of an aliphatic acid having 1 to 4 carbon atoms, and $R^9$ is the residue of an aliphatic alcohol having 2 to 20 carbon atoms. Most preferred precursors are those releasing an ester derived from acetic acid, i.e. wherein $R^8$ is —$CH_3$.

Other preferred precursors include compounds wherein $R^8$ is the residue of an aliphatic acid having 5 to 20 carbon atoms, and $R^9$ is the residue of an aliphatic alcohol having 1 to 5 carbon atoms. Most preferred compounds are those releasing an ester derived from ethanol, i.e. wherein $R^9$ is —$CH_2CH_3$.

Other preferred precursors include compounds wherein $R^8$ is the residue of an aliphatic acid having 1 to 4 carbon atoms, and $R^9$ is the residue of a terpene alcohol having 10 to 20 carbon atoms. Most preferred compounds are those wherein the alcohol is a monoterpene alcohol.

Other preferred precursors include compounds wherein $R^8$ is the residue of a cycloaliphatic acid having 5 to 20 carbon atoms, and $R^9$ is the residue of an aliphatic alcohol having 1 to 5 carbon atoms. Most preferred compounds are those wherein the alcohol is ethanol.

Other preferred precursors include compounds wherein $R^8$ is the residue of an aliphatic acid having 1 to 4 carbon atoms, and $R^9$ is the residue of an araliphatic alcohol having more than 5 carbon atoms. Most preferred precursors are those releasing an ester derived from acetic acid, wherein $R^8$ is —$CH_3$.

Other preferred precursors include compounds wherein at least one of the residues $R^6$ or $R^7$ is H. Most preferred are compounds wherein $R^6$ and $R^7$ is H. Upon cleavage of these precursors, a fragrant ketone of formula II is released wherein said ketone is an aryl methyl ketone.

Other preferred precursors include compounds wherein $R^6$ and $R^7$ are H, and $R^1$ to $R^5$ represent independently hydrogen, —$NO_2$, linear or branched $C_1$-$C_6$ alkyl, alkenyl, alkinyl, and $C_1$-$C_4$ alkoxy. Most preferred compounds are those releasing a fragrant ketone of formula II wherein the fragrant ketone is selected from 1-phenyl-ethanone, 2,4-dimethylphenyl-ethanone, 1-[4-(1,1-dimethylethyl)-2,6-dimethylphenyl]-ethanone, 1-(4-tert-butyl-3,5-dinitro-2,6-dimethyl)-ethanone and 1-(4-methoxyphenyl)-ethanone. Other preferred precursors include compounds wherein $R^1$ and $R^2$, $R^2$ and $R^3$, $R^3$ and $R^4$, $R^4$ and $R^5$ form together an aliphatic or aromatic ring, wherein this ring optionally contains substituted or unsubstituted $C_1$-$C_4$ alkyl, alkenyl, alkinyl residues and includes one or more oxygen atoms. Most preferred compounds are those releasing a fragrant ketone of formula II wherein the fragrant ketone is selected from 1-(2-naphtalenyl)-ethanone, 4-acetyl-6-tert-butyl-1,1-dimethyl-indan, 1-(5,6,7,8-tetrahydro-3,5,5,6,8,8-hexamethyl-2-naphthalenyl-ethanone, 1-(5,6,7,8-tetrahydro-3', 5', 5', 8', 8'-pentamethyl-2-naphthalenyl)-ethanone, 1-(5,6,7,8-tetrahydro-3'-ethyl-5', 5', 8', 8'-tetramethyl-2-naphthalenyl)-ethanone, 1-(2,3 -dihydro-1, 1,2,3,3 ,6-hexamethyl-1H-inden-5-yl-ethanone, 1-[2,3-dihydro-1,1 ,2,6-tetramethyl-3-(1-methylethyl-1H-inden-5-yl-ethanone, 5-acetyl-1,1,2,3,3-pentamethyl-indane, and 1-(5,6,7,8-tetrahydro-2-naphthalenyl)-ethanone.

Since the compounds of formula I, upon exposure to light, are cleaved and provide a fragrant ketone of formula II and a fragrant ester of formula III, they permit the development of useful consumer products with enhanced fragrant properties, especially having long lasting pleasant odors. Therefore, the present invention also relates to the use of all compounds of formula I as precursors for fragrant compounds.

The fragrance precursors of the present invention can be used in any product in which a prolonged and defined release of the above mentioned fragrant compounds is desired. Therefore, these precursors are especially useful in functional perfumery, and in products which are exposed to sunlight, during or after application.

The compounds of the present invention can act as fragrance precursors in functional and fine perfiunery, i.e. in fine fragrances, industrial, institutional, home, and personal care products. Industrial, institutional, and home cleaning products to which the fragrance precursors can be added include all kinds of detergents, window cleaners, hard surface cleaners, all purpose cleaners, and furniture polishes. The products can be liquids or solids, such as powders or tablets. Substrates including fabrics and surfaces treated with a product containing a fragrance precursor of the present invention will diffuse a fresh and clean odor upon exposure to light much longer than when cleaned with a conventional cleaner. Fabrics or clothes washed with such detergents will release the fragrant compounds even after having been stored for weeks in a dark place, e.g. a wardrobe.

The precursors of the present invention are also useful for application in all kinds of body care products. Especially interesting products are hair care products, for example, shampoos, conditioners, and hairsprays and skin care products such as cosmetic products, and especially sun protection products.

The above mentioned examples are of course only illustrative and non-limiting. Other products to which the precursors of the present invention may be added include soaps, bath and shower gels, deodorants, and even perfumes and colognes.

The fragrance precursors of the present invention can be used alone or in combination with other fragrance ingredients, solvents, or adjuvants known to those skilled in the art. Such ingredients are described, for example, in "Perfume and Flavor Chemicals," S. Arctander, Ed., Vol. I & II, Allured Publishing Corporation, Carol Stream, USA, 1994 and include fragrance compounds of natural or synthetic origin and essential oils of natural products.

The amounts in which the precursors of formula I are incorporated in the various above-mentioned products will vary. The amounts depend on the nature of the fragrant compounds to be released, the nature of the product to which the precursors are added, and the desired olfactory effect. The amounts used will also depend on the co-ingredients in a given composition when the precursors of the present invention are used in admixture with perfuming co-ingredients, solvents, or adjuvants. Typical concentrations are in the order of 0.01% to 5% by weight of the products.

The following examples are provided to further illustrate the process of the present invention. These examples are illustrative only and are not intended to limit the scope of the invention in any way.

EXAMPLES

In the examples that follow, the following chemicals were obtained from commnercial sources: bromo-acetonaphtone, bromo-acetanisole, sodium formate, trifluoroacetic acid, ethyl vinyl ether, mercury trifluoroacetate, 2-phenyl-ethanol, cis-3-hexenol, 3,5,5-trimethyl-hexanol, hexanol, 3-phenyl-propanol, citronellol, 3,7-dimethyl-3-octanol, 4-tert-butyl-cyclohexanol, and β-methoxy-styrene.

α-Bromo-Fixolide was prepared from Fixolide® according to R. M. Cowper, L. H. Davidson, *Org. Synth. Coll. Vol. II*, 1943, 480–481.
NMR: values of coupling constants J are given in Hertz (Hz).

Example 1

Preparation of Phenacyl Acetals

1. General procedure for the preparation of hydroxy-acetophenones

A suspension of the corresponding bromo-acetophenone (0.05 mmol) and sodium formate (17 g, 0.25 mol, 5 eq.) in aqueous ethanol (85%, 150 ml) was heated at reflux until completion of the reaction (TLC). Most of the ethanol was evaporated and 30 the mixture partitioned between MTBE (80 ml) and water (70 ml). The organic phase was separated and washed with aq. NaHCO$_3$ (sat.) and brine. Removal of the solvent in vacuo, after drying over MgSO$_4$, afforded a crude product as a solid which was recrystallized from ethanol.

2-Hydroxy-1-(4-methoxy-phenyl)-ethanone Obtained according to the general procedure.
mp 104–105° C.
$^1$H-NMR (400 MHz, CDCl$_3$):3.48(t,1H, J 4);4.82(d,2H, J 4);6.95-7.0 (m, 2H); 7.85–7.95(m, 2H).
IR (V$_{max}$, cm$^{-1}$, neat):3415m, 2929w, 1672s, 1603s. MS [m/z (EI)]:166(M$^+$, 4),155(100),77(28). 1-(3,5,5,6,8,8-Hexamethyl-5,6,7,8-tetrahydro-naphthalen-2-yl)-2-hydroxy-ethanone Obtained according to the general procedure.
mp 81–82° C.
$^1$H-NMR (400 MHz, CDCl$_3$):1.0(d,3H, J 6.8);1.08(s,3H);1.26(s,3H);1.31(s,3H); 1.33(s,3H);1.41(dd, 1H, J13.2, 2.4);1.63(dd,1H, J13.2, 13.2);1.8–1.95(m,1H); 2.54(s,3H);4.76(s,2H);7.26(s,1H);7.57(s,1H).
IR (V$_{max}$, cm$^{-1}$, neat):3447w, 2963m, 2911m, 1675s, 1607w.
MS [m/z (EI)]:274(M$^+$, 3), 243(100).
2-Hydroxy-1-naphthalen-2-yl-ethanone Obtained according to the general procedure.
mp 114–115° C. $^1$H-NMR (400 MHz, CDCl$_3$):3.59(t,1H, J4.4);5.02(d,2H, J4.4);7.55-7.7 (m,2H); 7.85–8.0(m,4H) ;8.43(s,1H).
IR (V$_{max}$, cm$^{-1}$, neat): 3428m, 3391m, 3051w, 2931w, 1680s, 1627m.
MS [m/z (EI)]:186(M$^+$, 12), 155(75),127(100), 40(26), 28(41).

2. General procedure for the preparation of alkyl vinyl ethers

A solution of the alcohol (0.1 mol) and mercury(II) trifluoroacetate (4 mmol, 0.04 eq.) in ethyl vinyl ether (50 ml, 1 mol, 5 eq.) was heated at reflux until completion of the reaction (TLC, GC). The ethyl vinyl ether was evaporated and the residue diluted with MTBE and poured into aq. NaHCO$_3$ (sat.). The separated aqueous phase was extracted with MTBE and the combined organic layers were washed with brine and dried over MgSO$_4$. After concentration, the crude oil was distilled under reduced pressure to afford the desired product as a colorless oil.

Hexyloxy-ethene Obtained according to the general procedure.
bp$_{170mbar}$ 89° C. $^1$H-NMR (400 MHz, CDCl$_3$):0.9(t,3H, J6.8);1.25-1.42(m,6H);1.6–1.7(m,2H); 3.67(t,2H, J6.8);3.96 (dd,1H, J6.8, 2);4.16(dd,1H, J14.4,2);6.46(dd,1H, J14.4, 6.8).
IR (V$_{max}$, cm$^{-1}$, neat): 3119w, 2957s, 2932s, 2861m, 1740w, 1636m, 1611s.
MS [m/z (EI)]:128 (M$^+$, 1),56(34),55(23),43(100),41(39).
(2-Vinyloxy-ethyl)-benzene Obtained according to the general procedure. $^1$H-NMR (400 MHz, CDCl$_3$):2.96(t,2H, J7.2);3.88-(t,2H, J7.2);3.99-(dd,1.H, J6.8, 2); 4.18(dd,1H, J14.4,2);6.46(dd,1H, J14.4,6.8);7.19–7.32(m,5H).
IR (V$_{max}$, cm$^{-1}$, neat): 3028m, 2947m, 2872m, 1636m, 1615s.
MS [m/z (EI)]:148 (M$^+$, 1),105(100),104(36),79(21),77(21).
(3,5,5-Trimethyl-hexyloxy)-ethene Obtained according to the general procedure.
bP$_{45mbar}$95° C. $^1$H-NMR (400 MHz, CDCl$_3$):0.9(s,9H);0.95 (d,3H, J6.4; 1.05–1.27(m,2H); 1.42–1.52(m,1H);1.6–1.7(m, 2H);3.68(t,2H, J6.4);3.96(dd,1H, J 7,2); 4.16(dd, 1H, J 15,2); 6.46(dd,1H, J 15,7).
IR (V$_{max}$, cm$^{-1}$, neat): 2955s, 2870m, 1647m, 1635m, 1610m.
MS [m/z (EI)]:170 (M$^+$, 1),71(23),70(24),69(21),57(100), 41 (22).
1-Vinyloxy-hex3(Z)-ene Obtained according to the general procedure.
bp$_{140mbar}$86° C. $^1$H-NMR (400 MHz, CDCl$_3$):0.97(t,3H, J 7.2);2.0–2.1(m,2H);2.37–2.45(m,2H); 3.68(t,2H, J 7.2); 3.98(dd,1H, J 6.8, 2); 4.18 (dd, 1H, J 14.4, 2); 5.3–5.4 (m, 1H); 5.47–5.55(m, 2H);6.46 (dd, 1H, J 14.4,6.8).
IR (V$_{max}$, cm$^{-1}$, neat): 3011w, 2965m, 2934m, 2874m, 1740w, 1636m, 1613m.
MS [m/z (EI)]: 126 (M$^+$, 1), 83 (21), 70 (45), 67 (34), 55 (100), 41 (45).
(1-Ethyl-1,5-dimethyl-hexyloxy)-ethene Obtained according to the general procedure.
bp$_{15mbar}$ 88–90° C.
$^1$H-NMR (400 MHz, CDCl$_3$): 0.85–0.9 (m, 9H); 1.12-1.6 (m, 9H); 1.18 (s, 3H); 4.01 (d, 1H, J6.4); 4.40 (dd, 1H, J 13.6, 0.4); 6.41 (dd, 1H, J 13.6, 6.4).
IR (v$_{max}$, cm$^{-1}$, neat): 3010w, 2940s, 2860m, 1625s.
MS [m/z (El): 184 (M$^+$, 1), 85 (51), 71 (59), 69 (20), 57 (100), 55 (31), 43 (83), 41 (32), 29 (23).
2,6-Dimethyl-8-vinyloxy-oct-2-ene Obtained according to the general procedure.
bp$_{15mbar}$ 98° C.
$^1$H-NMR (400 MHz, CDCl$_3$): 0.82 (d, 3H, J8); 1.05-1.7 (m, 5H); 1.51 (s, 3H); 1.59 (s, 3H); 1.8–2.0 (m, 2H); 3.57–3.65 (s, 2H); 3.87 (dd, 1H, J 8, 4); 4.07 (dd, 1H, J 16, 4); 4.97–5.05 (m, 1H); 6.37 (dd, 1H, J 16, 8).
IR (v$_{max}$, cm$^{-1}$, neat): 2960m, 2927w, 1636w, 1610m.
MS [m/z (EI)]: 182 (M$^+$, 1), 181 (1), 123 (22), 95 (36), 82(28), 81(37), 69 (100), 68 (22), 67 (33), 55 (47), 41 (64).
(3-Vinyloxy-propyl)-benzene Obtained according to the general procedure, after chromatography (SiO$_2$, EtOAc/Hexane) of the crude.
$^1$H-NMR (400 MHz, CDCl$_3$): 1.9–2.05 (m, 2H); 2.72 (t, 2H, J 7.6); 3.68 (t, 2H, J 6.4); 3.98 (dd, 1H, J 6.8, 2); 4.16 (dd, 1H, J 14.4, 2); 6.48 (dd, 1H, J 14.4, 6.8); 7.15–7.35 (m, 5H).
IR (v$_{max}$, cm$^{-1}$, neat): 3027w, 2946w, 2870w, 1636m, 1613s.
MS [m/z (El)]: 162 (M$^+$, 1), 118 (52), 117 (30), 91 (100).
1-t-Butyl-4-vinyloxy-cyclohexane Obtained according to the general procedure.
bp$_{15mbar}$ 95° C.
$^1$H-NMR (400 MHz, CDCl$_3$): 0.8–0.9 (m, 9H); 0.95–1.1 (m, 2H); 1.1–1.45 (m, 4H); 1.5–1.6 (m, 1H); 1.75–1.85 (m, 1H); 1.9–2.13 (m, 2H); 3.57–3.67 (m, 0.6H); 3.95–4.05 (m, 1.4H); 4.28 (dd, 1H, J 14, 1.2); 6.27–6.37 (m, 1H).
IR (v$_{max}$, cm$^{-1}$, neat): 2943s, 2865m, 1633m, 1607w.
MS [m/z (EI)]: 182 (M$^+$, 4), 83 (46), 69 (23), 57 (100), 55 (23), 41 (25).

3. General procedure for the preparation of phenacyl acetals (I, fragrance precursors)

To a suspension of the α-hydroxy-acetophenone (20 mmol) in toluene (10 ml) was added the alkyl vinyl ether (2 eq.), followed by trifluoroacetic acid (TFA) (2 or 3 drops, ~0.01 eq.). The mixture was heated at 50° C. When the reaction was finished (TLC), the reaction mixture was diluted with MTBE and poured into aq. NaHCO$_3$ (sat.). The aqueous phase was separated and extracted with MTBE, and the combined organic layers were washed with brine and dried over MgSO$_4$.

The crude, obtained after evaporation of the solvents, was purified by chromatography (SiO$_2$, EtOAc/Hexane) to afford the desired product as a colorless to pale yellow oil.

2-(1-Ethoxy-ethoxy)-1-(4-methoxy-phenyl)-ethanone (1) Obtained according to the general procedure without the use of solvent. No purification was required.
$^1$H-NMR (400 MHz, CDCl$_3$): 1.19 (t, 3H, J 7.2); 1.4 (d, 3H, J 5.2); 3.5–3.7 (m, 2H); 3.87 (s, 3H); 4.77 (m, 2H); 4.91 (q, 1H, J 5.6); 6.9–7.0 (m, 2H); 7.9–8.0 (m, 2H).
IR ($v_{max}$, cm$^{-1}$, neat): 2977w, 1693m, 1601s, 1576m, 1512.
UV [λ(ε), nm, CH$_2$Cl$_2$]: 219 (11796), 273 (17127).
MS [m/z (EI)]: 237 (M$^+$), 135 (100), 77 (26).

1-(4-Methoxy-phenyl)-2-(1-phenethyloxy-ethoxy)-ethanone (2) Obtained according to the general procedure without the use of solvent.
$^1$H-NMR (200 MHz, CDCl$_3$): 1.37 (d, 3H, J 5); 2.8–2.9 (m, 2H); 3.65–3.9 (m, 2H); 3.87 (s, 3H); 4.42–4.62 (m, 2H); 4.89 (q, 1H, J5); 6.87–6.95 (m, 2H); 7.1–7.3 (m, 5H); 7.75–7.85 (m, 2H).
IR ($v_{max}$, cm$^{-1}$, neat): 2987m, 2936m, 2840m, 1693s, 1601s, 1575m, 1512m.
UV [λ(ε), nm, CH$_2$Cl$_2$]: 276 (15042).
MS [m/z (EI)]: 314 (M$^+$), 150 (44), 135 (86), 105 (100), 77 (29). 2-(1-Hex-3(Z)-enyloxy-ethoxy)-1-(4-methoxy-phenyl)-ethanone (3) Obtained according to the general procedure without the use of solvent.
$^1$H-NMR (200 MHz, CDCl$_3$): 0.95 (t, 3H, J 7.5); 1.4 (d, 3H, J 6); 1.95–2.15 (m, 2H); 2.25–2.4 (m, 2H); 3.4–3.7 (m, 2H); 3.87 (s, 3H); 4.8 (m, 2H); 4.92 (q, 1H, J 6); 5.25–5.55 (m, 2H); 6.9–7.0 (m, 2H); 7.9–8.0 (m, 2H).
IR ($v_{max}$, cm$^{-1}$, neat): 2963m, 2934m, 2874m, 1695m, 1602s, 1576m, 1512m.
UV [λ(ε), nm, CH$_2$Cl$_2$]: 219 (11211), 273 (16231).
MS [m/z (EI)]: 292 (M$^+$, 1), 150 (27), 135 (100), 83 (75), 55 (57).

1-(4-Methoxy-phenyl)-2-[1-(3,5,5-trimethyl-hexyloxy)-ethoxyl]-ethanone (4) Obtained according to the general procedure without the use of solvent.
$^1$H-NMR (200 MHz, CDCl$_3$): 0.8–0.95 (m, 3H); 0.86 (s, 9H); 1.0–1.35 (m, 3H); 1.41 (d, 3H, J 5); 1.45–1.7 (m, 2H); 3.4–3.7 (m, 2H); 3.89 (s, 3H); 4.65–4.7 (m, 2H); 4.9 (q, 1H, J 5); 5.05–5.1 (m, 1H); 6.9–7.0 (m, 2H); 7.9–8.0 (m, 2H).
IR ($v_{max}$, cm$^{-1}$, neat): 2954s, 1695m, 1602s, 1576m, 1512m.
UV [λ(ε), nm, CH$_2$Cl$_2$]: 219 (10941), 273 (15481).
MS [m/z (EI)]: 336 (M$^+$), 135 (73), 71 (24), 70 (22), 69 (21), 57 (100), 41 (22).

2-(1-Hexyloxy-ethoxy)-1-(4-methoxy-phenyl)-ethanone (5) Obtained according to the general procedure, but using Montmorillonite® in refluxing toluene instead of TFA.
$^1$H-NMR (200 MHz, CDCl$_3$): 0.8–1.0 (m, 3H); 1.1–1.7 (m, 11H); 3.4–3.7 (m, 2H); 3.89 (s, 3H); 4.7–4.8 (m, 2H); 4.91 (q, 1H, J 6.2); 6.9–7.0 (m, 2H); 7.9–8.0 (m, 2H).
IR ($v_{max}$, cm$^{-1}$, neat): 2932s, 2859m, 1694m, 1601m, 1576m, 1512s.
UV [λ(ε), nm, CH$_2$Cl$_2$]: 219 (10656), 276 (15203).
MS [m/z (EI)]: 294 (M$^+$), 135 (93), 85 (21), 56 (35), 55 (24), 43 (100), 41 (36).

1-(4-Methoxy-phenyl)-2-[1-(3-phenyl-propoxy)-ethoxy]-ethanone (6) Obtained according to the general procedure without the use of solvent.
$^1$H-NMR (400 MHz, CDCl$_3$): 1.4 (d, 3H, J 5.2); 1.85–1.9 (m, 2H); 2.65–2.7 (m, 2H); 3.45–3.65 (m, 2H); 3.86 (s, 3H); 4.76 (m, 2H); 4.9 (q, 1H, J 5.2); 6.9–7.0 (m, 2H); 7.1-7.3 (m, 5H); 7.9–8.0 (m, 2H).
IR ($v_{max}$, cm$^{-1}$, neat): 2936w, 1693m, 1600s, 1575m, 1511m.
UV [λ(ε), nm, CH$_2$Cl$_2$]: 217 (18180), 273 (18826).
MS [m/z (EI)]: 328 (M$^+$), 135 (51), 118 (45), 117 (29), 92 (20), 91 (100), 77 (22).

2-[1-(3,7-Dimethyl-oct-6-enyloxy)-ethoxy]-1-(4-methoxy-phenyl)-ethanone (7) Obtained according to the general procedure.
$^1$H-NMR (400 MHz, CDCl$_3$): 0.8–0.95 (m, 3H); 1.1–1.2 (m, 1H); 1.25–1.45 (m, 5H); 1.5–1.7 (m, 8H); 1.9–2.05 (m, 2H); 3.45–3.7 (m, 2H); 3.87 (s, 3H); 4.7–4.82 (m, 2H); 4.9 (q, 1H, J 5.6); 5.05–5.1 (m, 1H); 6.9–7.0 (m, 2H); 7.9–8.0 (m, 2H).
IR ($v_{max}$, cm$^{-1}$, neat): 3534w, 2914m, 1694m, 1601s, 1576m, 1511m.
UV [λ(ε), nm, CH$_2$Cl$_2$]: 218 (13546), 273 (18063). MS [m/z (EI)]: 348 (M$^+$), 193 (42), 135 (100), 121 (31), 83 (29), 81 (24), 69 (60), 41 (22).

1-(3,5,5,6,8,8-Hexamethyl-5,6,7,8-tetrahydro-naphthalen-2-yl)-2-(1-hexyloxy-ethoxy)-ethanone (8) Obtained according to the general procedure without the use of solvent.
$^1$H-NMR (400 MHz, CDCl$_3$): 0.87 (t, 3H, J 7.2); 0.99 (d, 3H, J 6.9); 1.06 (s, 3H); 1.15-1.45 (m, 20H); 1.5–1.7 (m, 2H); 1.8–1.95 (m, 1H); 2.48 (s, 3H); 3.4–3.65 (m, 2H); 4.68 (m, 2H); 4.89 (q, 1H, J 5.2); 7.21 (s, 1H); 7.55 (s, 1H).
IR ($v_{max}$, cm$^{-1}$, neat): 2960m, 2929m, 2871m, 1681m, 1607w, 1544w.
UV [λ(ε), nm, CH$_2$Cl$_2$]: 217 (20110), 257 (11478).
MS [m/z (EI)]: 402 (M$^+$), 243 (100), 85 (22), 43 (24).

1-(3,5,5,6,8,8-Hexamethyl-5,6,7,8-tetrahydro-naphthalen-2-yl)-2-(1-hex-3(Z)-enyloxy-ethoxy)-ethanone (9) Obtained according to the general procedure without the use of solvent. No purification was required.
$^1$H-NMR (400 MHz, CDCl$_3$): 0.95 (t, 3H, J 6.8); 0.99 (d, 3H, J 6.8); 1.07 (s, 3H); 1.15-1.45 (m, 12H); 1.6–1.7 (m, 2H); 1.8–1.95 (m, 1H); 2.0–2.1 (m, 2H); 2.25–2.35 (m, 2H); 2.48 (s, 3H); 3.4–3.7 (m, 2H); 4.69 (m, 2H); 4.91 (q, 1H, J 5.2); 5.3–5.5 (m, 2H); 7.21 (s, 1H); 7.54 (s, 1H).
IR ($v_{max}$, cm$^{-1}$, neat): 2963s, 2931m, 1681m, 1608w, 1544w.
UV [λ(ε), nm, CH$_2$Cl$_2$]: 216 (21722), 258 (12495), 295 (2228). MS [m/z (EI)]: 400 (M$^+$, 1), 243 (100), 83 (28), 55 (24).

2-(1-Ethoxy-ethoxy)-1-(3,5,5,6,8,8-hexamethyl-5,6,7,8-tetrahydro-naphthalen-2-yl)-ethanone (10) Obtained according to the general procedure without the use of solvent.
$^1$H-NMR (400 MHz, CDCl$_3$): 0.94 (d, 3H, J 6.8); 1.0 (s, 3H); 1.15–1.45 (m, 15H); 1.55–1.7 (m, 2H); 1.8–1.95 (m, 1H); 2.47 (s, 3H); 3.5–3.75 (m, 2H); 4.68 (m, 2H); 4.89 (q, 1H, J 5.6); 7.21(s, 1H); 7.55 (s, 1H).
IR ($v_{max}$, cm$^{-1}$, neat): 2964s, 2929m, 1681m, 1607w, 1544w.
UV [λ(ε), nm, CH$_2$Cl$_2$]: 217 (20799), 257 (11635).
MS [m/z (EI)]: 346 (M$^+$), 243 (100).

2-(1-Hexyloxy-ethoxy)-1-naphthalen-2-yl-ethanone (11) Obtained according to the general procedure.
$^1$H-NMR (400 MHz, CDCl$_3$): 0.86 (t, 3H); 1.2-1.4 (m, 6H); 1.43 (d, 3H, J 5.2); 1.5–1.6 (m, 2H); 3.45–3.7 (m, 2H); 4.9–5.02 (m, 3H); 7.52-7.65 (m, 2H); 7.85-8.05 (m, 4H); 8.47 (s, 1H).

IR ($v_{max}$, cm$^{-1}$, neat): 2930m, 2858w, 1697m, 1628w.
UV [λ(ε), nm, CH$_2$Cl$_2$]: 250 (51217), 285 (9882).
MS [m/z (EI)]: 314 (M$^+$), 155 (100), 127 (87), 56 (22), 43 (67), 41 (23).

2-[1-(3,7-Dimethyl-oct-6-enyloxy)-ethoxy-]1-naphthalen-2-yl-ethanone (12) Obtained according to the general procedure. $^1$H-NMR (400 MHz, CDCl$_3$): 0.8–0.95 (m, 3H); 1.1-1.2 (m, 1H); 1.25–1.5 (m, 2H); 1.43 (d, 3H, J 5.6); 1.5–1.7 (m, 8H); 1.57 (s, 3H); 1.66 (s, 3H); 1.85–2.05 (m, 2H); 3.45–3.75 (m, 2H); 4.9–5.0 (m, 3H); 5.02–5.1 (m, 1H); 7.52-7.65 (m, 2H); 7.85–8.05 (m, 4H); 8.47 (s, 1H).
IR ($v_{max}$, cm$^{-1}$, neat): 2914m, 1698m, 1623w, 1597w.
UV [λ(ε), nm, CH$_2$Cl$_2$]: 250 (51252), 285 (9760).
MS [m/z (EI)]: 368 (M$^+$), 213 (26), 155 (83), 142 (26), 127 (26), 83 (54), 81 (31), 69 (100), 57 (28), 55 (24), 41 (35).

2-[1-(1-Ethyl-1,5-dimethyl-hexyloxy)-ethoxy]-1-naphtalen-2-yl-ethanone (13) Obtained according to the general procedure.
$^1$H-NMR (400 MHz, CDCl$_3$): 0.8–0.9 (m, 9H); 1.1–1.65 (m, 15H); 4.9–5.02 (m, 2H); 5.27 (m, 1H); 7.55–7.65 (m, 2H); 7.85–8.05 (m, 4H); 8.49 (s, 1H).
IR ($v_{max}$, cm$^{-1}$, neat): 3520w, 2951m, 1699s, 1628m, 1597w.
UV [λ(ε), mn, CH$_2$Cl$_2$]: 250 (54132), 284 (10278).
MS [m/z (EI)]: 370 (M$^+$, 2), 213 (32), 156 (21), 155 (100), 141 (55), 127 (65), 85 (53), 71 (60), 69 (23), 57 (74), 55 (32), 43 (74), 41 (34).

2-[1-(4-t-Butyl-cyclohexyloxy)-ethoxy]-1-naphtalen-2-yl-ethanone (14) Obtained according to the general procedure. The two diastereoisomers could be separated by chromatography. trans-isomer: $^1$H-NMR (400 MHz, CDCl$_3$): 0.82 (s, 9H); 0.9-1.05 (m, 3H); 1.15–1.35 (m, 2H); 1.42 (d, 3H, J 2.1); 1.7-1.8 (m, 2H); 1.95-2.1 (m, 2H); 3.75–3.6 (m, 1H); 4.95 (m, 2H); 5.1 (q, 1H); 7.5–7.65 (m, 2H); 7.85–8.05 (m, 4H); 8.5 (s, 1H). cis-isomer:
$^1$H-NMR (400 MHz, CDCl$_3$): 0.84 (s, 9H); 0.95-1.05 (m, 2H); 1.25–1.55 (m, 6H); 1.75–2.05 (m, 4H); 3.9–3.95 (m, 1H); 4.95 (m, 2H); 5.02 (q, 1H); 7.5–7.65 (m, 2H); 7.85–8.05 (m, 4H); 8.5 (s, 1H).
IR ($v_{max}$, cm$^{-1}$, neat): 2939m, 2865m, 1698m, 1628w.
UV [λ(ε), nm, CH$_2$Cl$_2$]: 251 (43232), 287 (8289).
MS [m/z (EI)]: 368 (M$^+$), 170 (28), 155 (39), 139 (38), 127 (31), 83 (53), 57 (100), 41 (27).

1-(4-Methoxy-phenyl)-2-(1-methoxy-2-phenyl-ethoxy)-ethanone (15) Obtained according to the general procedure without the use of solvent.

$^1$H-NMR (400 MHz, CDCl$_3$): 3.0–3.05 (m, 2H); 3.35 (s, 3H); 3.88 (s, 3H); 4.76 (m, 2H); 4.8–4.85 (m, 1H); 6.9-6.95 (m, 2H); 7.15–7.25 (m, 5H); 7.9–7.95 (m, 2H).
IR ($v_{max}$, cm$^{-1}$, neat): 2933 m, 2838m, 1692m, 1600s, 1575m, 1511s.
UV [λ(ε), nm, CH$_2$Cl$_2$]: 218 (17292), 277 (13404).
MS [m/z (EI)]: 300 (M$^+$), 209 (26), 149 (34), 135 (100), 134 (21), 121 (46), 91 (43), 77 (24).

Example 2

Photolysis of Phenacyl Acetals (I) in Solutions

Photorelease assays were conducted on solutions (typical concentrations of precursors (I): 0.05% to 0.1% g/v) in organic solvents (preferably ethanol) or on cotton towels after deposition of the phenacyl acetals (I), as described below in the example 3.

The solutions were irradiated with a mercury lamp (150 W) in a borosilicate glass apparatus (Pyrex®) so as to limit the irradiation window to mainly the UVA and UVB spectrum of sun light. The alcoholic solution was irradiated for one hour and samples taken every 15 minutes to analyze the extent of the photolysis.

Analysis

The presence of the aryl ketone (II) and ester (III) after photolysis in solutions was determined by using GC retention times. Samples (0.2 μl) were injected (on column injection) without further dilution. Gas chromatography-flame ionization detection (GC-FID) was carried out with a Fisons-GC 8000 series apparatus, using a J&W Scientific DB-5 capillary column (30 m, 0.32 mm id, 0.25 μm film, He carrier gas, 85 kPa). The results are summarized in table 1.

Figure 2:
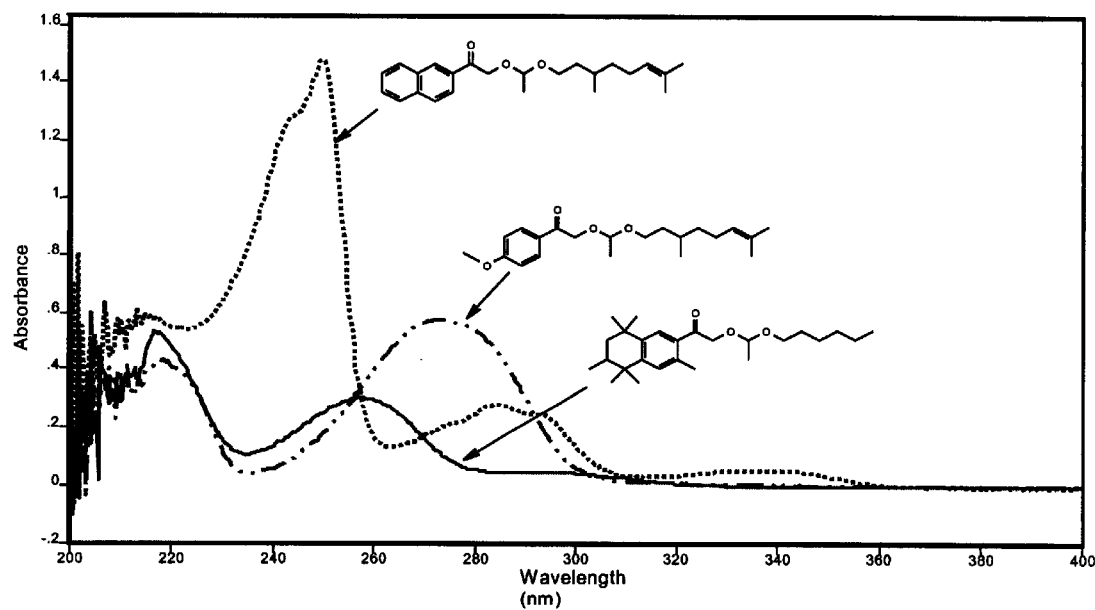

Whereas precursors derived from Oranger Crystals® cleaved fairly slowly (FIG. 1), those derived from acetanisole cleaved fast and Fixolide® precursors even faster. The estimated half lives under the said conditions were inferred from the curves given in FIG. 1. The rates are calculated from the GC analysis (corresponding peak area). Representative UV spectra are shown in FIG. 2. $t_{1/2}$ (Fixolide®)=15 minutes $t_{1/2}$ (Acetanisole)=20–30 minutes $t_{1/2}$ (Oranger Crystals®)=50–60 minutes

TABLE 1

Release of aryl ketones (II) and esters (III) from phenacyl acetals (I) in solution upon irradiation with a mercury lamp

| | Fragrance Target | | |
| --- | --- | --- | --- |
| STRUCTURE (I) | aryl ketone (II) | ester (III) | UV-test* |
| 1 | acetanisole | (ethyl acetate) | ++ |

TABLE 1-continued

Release of aryl ketones (II) and esters (III) from phenacyl acetals (I) in solution upon irradiation with a mercury lamp

| STRUCTURE (I) | Fragrance Target | | UV-test* |
|---|---|---|---|
| | aryl ketone (II) | ester (III) | |
| 2 | acetanisole | phenethyl acetate | ++ |
| 3 | acetanisole | cis-3-hexenyl acetate | ++ |
| 4 | acetanisole | nonanyl acetate | ++ |
| 5 | acetanisole | hexyl acetate | ++ |
| 6 | acetanisole | phenylpropyl acetate | ++ |
| 7 | acetanisole | citronellyl acetate | ++ |
| 8 | Fixolide ® | hexyl acetate | +++ |

TABLE 1-continued

Release of aryl ketones (II) and esters (III) from phenacyl acetals (I) in solution upon irradiation with a mercury lamp

| STRUCTURE (I) | Fragrance Target | | UV-test* |
|---|---|---|---|
| | aryl ketone (II) | ester (III) | |
| 9 | Fixolide ® | cis-3-hexenyl acetate | +++ |
| 10 | Fixolide ® | (ethyl acetate) | +++ |
| 11 | Oranger Crystals ® | hexyl acetate | + |
| 12 | Oranger Crystals ® | citronellyl acetate | + |
| 15 | acetanisole | methyl phenyl-acetate | ++ |

*0: no cleavage, +: slow cleavage, ++: medium cleavage, +++: fast cleavage

Example 3

Spray Tests 1 g of an approximately 0.2% phenacyl acetal (I) solution in ethanol was evenly sprayed on a Terry towel (white cotton towel, 25 cm ×25 cm, 45 g), corresponding to 45–75 μg/g cotton. The sprayed towels were allowed to dry in a dark and odorless place. When dry, the towels were irradiated for a few seconds up to a few minutes with a tanning lamp (Osram Ultra-Vitalux®, 300 W; at a distance of 50 cm, the light has approximately six to seven times the effect of the natural sunlight at noon on a sea-side mid-summer day). The evaluation was done by a trained panel of perfumers before and after irradiation. Before irradiation, the towels were judged to be odorless. The results after irradiation are summarized in table 2.

TABLE 2

Release of aryl ketones (II) and esters (III) from phenacyl acetals (I) on fabrics
upon irradiation with a tanning lamp

| STRUCTURE (I) | Fragrance Target (perception)* | | Global appreciation* |
|---|---|---|---|
| | aryl ketone (II) | ester (III) | |
| 1 | acetanisole (++) | ethyl acetate (0) | + |
| 2 | acetanisole (++) | phenethyl acetate (+++) | +++ |
| 3 | acetanisole (++) | cis-3-hexenyl acetate (++) | ++ |
| 4 | acetanisole (++) | nonanyl acetate (+) | + |
| 5 | acetanisole (++) | hexyl acetate (++) | ++ |
| 6 | acetanisole (++) | phenylpropyl acetate (++) | ++ |
| 7 | acetanisole (++) | citronellyl acetate (+) | ++ |
| 8 | Fixolide ® (++) | hexyl acetate (+++) | +++ |

TABLE 2-continued

Release of aryl ketones (II) and esters (III) from phenacyl acetals (I) on fabrics upon irradiation with a tanning lamp

| STRUCTURE (I) | Fragrance Target (perception)* | | Global appreciation* |
|---|---|---|---|
| | aryl ketone (II) | ester (III) | |
| 9 | Fixolide ® (++) | cis-3-hexenyl acetate (+++) | +++ |
| 10 | Fixolide ® (++) | ethyl acetate (0) | ++ |
| 11 | Oranger Crystals ® (++) | hexyl acetate (++) | ++ |
| 12 | Oranger Crystals ® (++) | citronellyl acetate (+) | ++ |
| 13 | Oranger Crystals ® (++) | tetrahydro linalyl acetate (++) | +++ |
| 14 | Oranger Crystals ® (++) | t-butyl-cyclohexyl acetate (+) | + |
| 15 | acetanisole (++) | methyl phenyl acetate (+) | + |

*0: very weak, +: weak, ++: medium, +++: strong

Example 4
Stability Tests

The phenacyl acetals (I) were incubated in aqueous buffer solutions of pH 2.5, pH 7 and pH 9.5 for 24 h at 37° C. and were found to be stable in basic and neutral media, but less so under acidic conditions. The results are summarized in table 3.

TABLE 3

Stability of phenacyl acetals (III) under different pH

| STRUCTURE (I) | pH 2.5 | pH 7 | pH 9.5 | pH 11* |
|---|---|---|---|---|
| 1 | unstable | stable | stable | not tested |
| 2 | unstable | stable | stable | stable |
| 3 | unstable | stable | stable | stable |
| 4 | unstable | stable | stable | stable |
| 5 | unstable | stable | stable | stable |
| 6 | unstable | stable | stable | stable |
| 8 | stable | stable | stable | stable |

TABLE 3-continued

Stability of phenacyl acetals (III) under different pH

| STRUCTURE (I) | pH 2.5 | pH 7 | pH 9.5 | pH 11* |
|---|---|---|---|---|
| 9 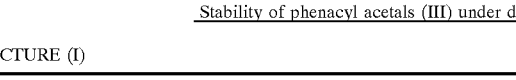 | stable | stable | stable | stable |

*The results at pH 11 were determined under washing conditions as described in the example 5 below.

Example 5

Hand Washing Tests

Washing tests were performed according to the following hand washing test cedure with OMO Progress® base which contains the following ingredients:

| | |
|---|---|
| LAS | 22.0% |
| STP | 13.3% |
| CP5 (as 100%) | 1.5% |
| SCMC (as 100%) | 0.34% |
| Fluorescer (E1/1) | 1.41 |
| Savinase | 1.15% |
| Lipolase | 0.15% |
| Amilase | 0.30% |
| Perborate | 8.0% |
| TAED | 2.4% |
| Alkalinity (pH) | 14.4 |

1- The washing powder (2.1 g) containing the phenacyl acetal (I, about 21 mg, 1%) was dissolved in water (500 ml) at room temperature.

2- The towels (35 g) were added to the liquor and mixed with a glass stick.

3- Towels were soaked for 45 minutes with stirring every 15 minutes.

4- The wringed towels were rinsed three times with fresh water (250 ml) with intermediate wringing.

5- Towels were allowed to dry in a dark and odorless place before analysis or evaluation.

Analysis

The towels were extracted with an organic solvent (preferably t-butyl methyl ether) using a Dionex ASE200 Accelerated Solvent Extractor and the extracts were analyzed by HPLC (Hewlett Packard Series 1100, column: Zorbax Eclipse XDB-C18, dimensions 15 cm×4.6 mm×5 $\mu$m).

The washing liquor was extracted with an organic solvent (preferably t-butyl methyl ether, 250 ml) and analyzed by HPLC as above.

Stability in washing liquor:

The washing liquor (2.1 g washing powder containing 1% phenacyl acetal (I) in 500 ml water), according to 1 in the above described washing procedure, was stirred during one hour at room temperature. Extraction with an organic solvent (preferably t-butyl methyl ether) to recover organic compounds and analysis with HPLC gave the amounts of recovered phenacyl acetal (I), table 4.

TABLE 4

Stability of phenacyl acetals (I) under washing conditions

| STRUCTURE | Amount incorporated (mg) | Amount ecovered (mg) | Recovered (mg) |
|---|---|---|---|
| 2 | 22.3 | 18.5 | 83 (±10) |
| 3 | 21 | 22.3 | 100 (±10) |

TABLE 4-continued
Stability of phenacyl acetals (I) under washing conditions
| STRUCTURE | Amount incorporated (mg) | Amount recovered (mg) | Recovered (mg) |
|---|---|---|---|
| 4 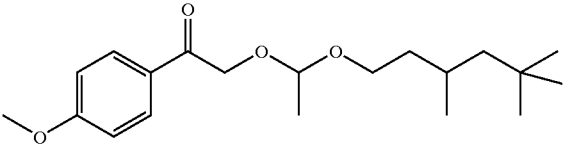 | 21.9 | 23.5 | 100 (±10) |
| 5 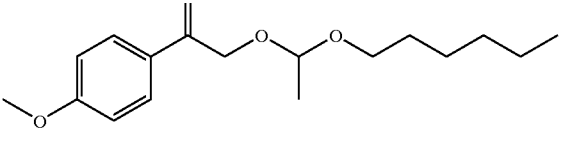 | 24.4 | 25.7 | 100 (±10) |
| 6 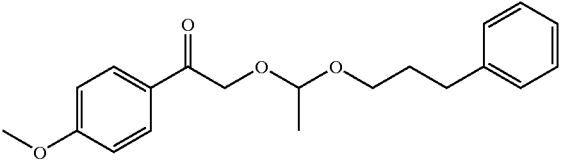 | 22.2 | 20.8 | 94 (±10) |
| 8 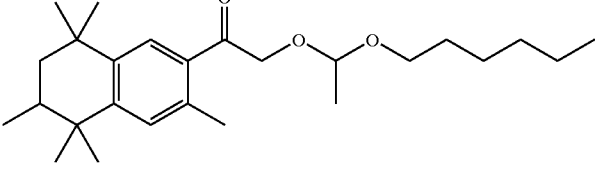 | 22.5 | 22.2 | 99 (±10) |
| 9 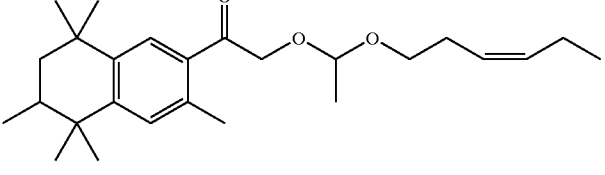 | 20.8 | 20.0 | 96 (±10) |

Washing:

The dried towels, taken from the described hand washing procedure, were either irradiated with the previously mentioned tanning lamp and olfactively evaluated or analyzed by HPLC.

The aqueous liquors were extracted with an organic solvent (preferably t-butyl methyl ether) and analytical HPLC gave the results in table 5, which are related to partition between water and fabric.

TABLE 5

Partition between water and fabric (substantivity) of phenacyl acetals (I)

| STRCUTURE (I) | Amount incorporated (mg) | Water mg | % (±10%) | Towel extract mg | % (±10%) |
|---|---|---|---|---|---|
| 2 | 23.9 | 15 | 63% | 10.5 | 44% |
| 3 | 22.6 | 13.3 | 59% | 14 | 62% |
| 4 | 23.2 | 17.5 | 75% | 8.9 | 38% |
| 5 | 25.2 | 18.4 | 73% | 11.7 | 46% |
| 6 | 22.2 | 14.5 | 65% | 17 | 47% |
| 8 | 20.6 | 16.3 | 69% | 8.7 | 42% |
| 9 | 22.8 | 15.3 | 67% | 10.3 | 45% |

The invention being thus described, it will be obvious that the same may be varied in many ways. Such variations are not to be regarded as a departure from the spirit and scope of the invention and all such modifications are intended to be included within the scope of the following claims.

What is claimed is:

1. A fragrance precursor of formula I:

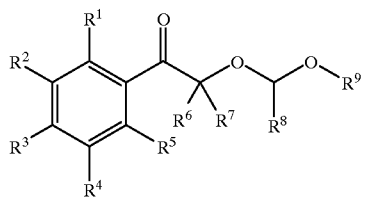

for a fragrant ketone of formula II:

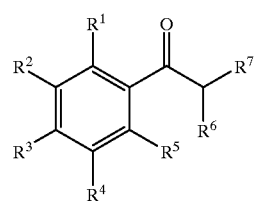

and a fragrant ester of formula III:

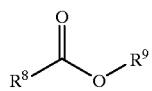

wherein, $R^1$ to $R^5$ represent independently H, —$NO_2$, linear or branched $C_1$–$C_6$-alkyl, $C_1$–$C_6$-alkenyl, $C_1$–$C_6$-alkinyl or $C_1$–$C_4$-alkoxy, $R^1$ and $R^2$, $R^2$ and $R^3$, $R^3$ and $R^4$ and $R^4$ and $R^5$ may form together one or two aliphatic or aromatic rings, these rings may optionally contain linear or branched $C_1$–$C_4$-alkyl, $C_1$–$C_4$-alkenyl or $C_1$–$C_4$-alkinyl residues, and the above rings and residues may comprise one or more oxygen atoms, $R^6$ and $R^7$ are independently H, linear or branched $C_1$–$C_6$-alkyl-, $C_1$–$C_6$-alkenyl, $C$ -$C_6$-alkinyl, and $R^6$ or $R^7$ may form with either $R^1$ or $R^5$ a carbocyclic ring optionally substituted by an aliphatic residue, $R^8$ is the residue of an aliphatic acid having 1 to 4 carbon atoms and $R^9$ is the residue of an aliphatic alcohol having 2 to 20 carbon atoms.

2. A fragrance precursor according to claim 1 wherein $R^8$ in formula I is —$CH_3$ and $R^9$ is the residue of an aliphatic alcohol having 2 to 20 carbon atoms.

3. A fragrance precursor according to claim 1 wherein $R^8$ in formula I is the residue of an aliphatic acid having 5 to 20 carbon atoms and $R^9$ is the residue of an aliphatic alcohol having 1 to 5 carbon atoms.

4. A fragrance precursor according to claim 1 wherein $R^8$ in formula I is the residue of an aliphatic acid having 5 to 20 carbon atoms and $R^9$ is —$CH_2CH_3$.

5. A fragrance precursor according to claim 1 wherein $R^8$ in formula I is the residue of an aliphatic acid having 1 to 4 carbon atoms and $R^9$ is the residue of a terpene alcohol having 10 to 20 carbon atoms.

6. A fragrance precursor according to claim 1 wherein $R^8$ in formula I is the residue of an aliphatic acid having 1 to 4 carbon atoms and $R^9$ is the residue of a monoterpene alcohol.

7. A fragrance precursor according to claim 1 wherein $R^8$ in formula I is the residue of a cycloaliphatic acid having 5 to 20 carbon atoms and $R^9$ is the residue of an aliphatic alcohol having 1 to 5 carbon atoms.

8. A fragrance precursor according to claim 1 wherein $R^8$ in formula I is the residue of a cycloaliphatic acid having 5 to 20 carbon atoms and $R^9$ is —$CH_2$ $CH_3$.

9. A fragrance precursor according to claim 1 wherein $R^8$ in formula I is the residue of an aliphatic acid having 1 to 4 carbon atoms and $R^9$ is the residue of an araliphatic alcohol having more than 5 carbon atoms.

10. A fragrance precursor according to claim 1 wherein $R^8$ in formula I is —$CH_3$ and $R^9$ is the residue of an araliphatic alcohol having more than 5 carbon atoms.

11. A fragrance precursor according to claim 1 wherein at least one of the residues $R^6$ and $R^7$ in formula I is H.

12. A fragrance precursor according to claim 1 wherein the residues $R^6$ and $R^7$ in formula I are H.

13. A fragrance precursor according to claim 1 wherein in formula I $R^6$ and $R^7$ are H and $R^1$ to $R^5$ represent independently H, —$NH_2$, linear or branched $C_1$–$C_{6\text{-}alkyl}$, $C_1$–$C_4$ alkoxy.

14. A fragrance precursor according to claim 1 wherein the fragrant ketone of formula II is selected from the group consisting of 1-phenyl-ethanone, 2,4-dimethylphenyl-ethanone, 1-[4-(1,1-dimethylethyl)-2,6-dimethylphenyl]-ethanone, 1-(4-tert-butyl-3,5-dinitro-2,6-dimethyl)-ethanone, and 1-(4-methoxyphenyl)-ethanone.

15. A fragrance precursor according to claim 1 wherein in formula I $R^1$ and $R^2$, $R^2$ and $R^3$, $R^3$ and $R^4$, or $R^4$ and $R^5$, form together an aliphatic or aromatic ring.

16. A fragrance precursor according to claim 21 wherein the aliphatic or aromatic ring contains substituted or unsubstituted $C_1$ –$C_4$-alkyl, $C_1$ -$C_4$-alkenyl, or $C_1$-$C_4$-alkinyl residues.

17. A fragrance precursor according to claim 21 wherein the aliphatic or aromatic ring comprises one or more oxygen atoms.

18. A fragrance precursor according to claim 1 wherein the fragrant ketone of formula II is selected from the group consisting of 1-(2-naphtalenyl)-ethanone, 4-acetyl-6-tert-butyl- 1,1 -dimethyl-indan, 1 -(5,6,7,8-tetrahydro-3,5,5,6,8, 8-hexamethyl-2-naphthalenyl-ethanone, 1-(5,6,7,8-tetrahydro-3', 5', 5', 8', 8'-pentamethyl-2-naphthalenyl)-ethanone, 1-(5,6,7,8-tetrahydro-3'-ethyl-5'- 5', 8', 8'-tetramethyl-2-naphthalenyl)-ethanone, 1 -(2,3-dihydro-1, 1,2,3,3,6-hexamethyl-1H-inden-5-yl-ethanone, 1-[2,3-dihydro-1,1,2,6-tetramethyl-3-(1-methylethyl-1H-inden-5-yl-ethanone, 5-acetyl-1,1,2,3,3-pentamethyl-indane, and 1-(5,6,7,8-tetrahydro-2-naphthalenyl)-ethanone.

19. A compound of formula I:

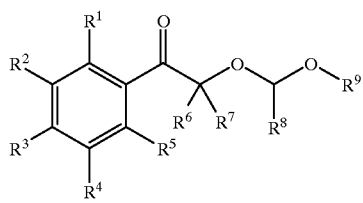
(I)

wherein, $R^1$ to R5 represent independently H, $-NO_2$, linear or branched $C_1-C_6$-alkyl, $C_1-C_6$-alkenyl, $C_1-C_6$-alkinyl, or $C_1-C_4$-alkoxy, $R^1$ and $R^2$, $R^2$ and $R^3$, $R^3$ and $R^4$, and $R^4$ and $R^5$ form together one or two aliphatic or aromatic rings, $R^6$ and $R^7$ are independently H, linear or branched $C_1-C_6$-alkyl, $C_1-C_6$-alkenyl, $C_1-C_6$-alkinyl, and $R^8$ and $R^9$ are the residues of an acid and an alcohol respectively, which together form a fragrant ester.

20. A compound according to claim 19 wherein $R^1$ and $R^2$, $R^2$ and $R^3$, $R^3$ and $R^4$, and $R^4$ and $R^5$ form together one or two aliphatic or aromatic rings and these rings contain linear or branched, substituted or unsubstituted $C_1-C_4$-alkyl, $C_1-C_4$-alkenyl or $C_1-C_4$-alkinyl residues.

21. A compound according to claim 19 wherein the rings comprise one or more oxygen atoms.

22. A compound according to claim 19 wherein $R^6$ or $R^7$ form with either $R^1$ or $R^5$ a substituted or unsubstituted carbocyclic ring.

23. A fragrance precursor of formula I:

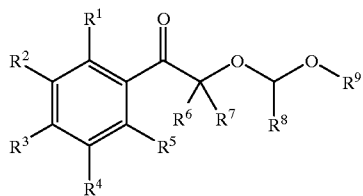
(I)

for a fragrant ketone of formula II:

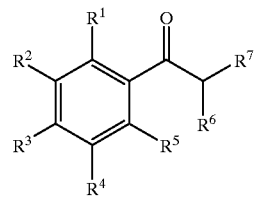
(II)

and a fragrant ester of formula III:

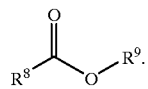
(III)

wherein, $R^1$ to $R^5$ represent independently H, $-NO_2$, linear or branched $C_1-C_6$-alkyl, $C_1-C_6$-aklenyl, $C_1-C_6$-alkinyl or $C_1-C_4$-alkoxy, $R^1$ and $R^2$ and $R^3$ and $R^4$ and $R^4$ and $R^5$ may form together one or two aliphatic or aromatic rings, these rings may optionally contain linear or branched $C_1-C_4$-alkyl, $C_1-C_4$-alkenyl or $C_1-C_4$-alkinyl residues, and the above rings and residues may comprise one or more oxygen atoms, $R^6$ and $R^7$ are independently H, linear or branched $C_1-C_6$-alkyl-, $C_1-C_6$-alkenyl, $C_1-C_6$-alkinyl, and $R^6$ or $R^7$ may form with either $R^1$ or $R^5$ a carbocyclic ring optionally substituted by an aliphatic residue, $R^8$ in formula I is the residue of an aliphatic acid having 1 to 20 carbon atoms, and $R^9$ in formula I is the residue of an aliphatic alcohol having 1 to 20 carbon atoms.

24. A fragrance precursor according to claim 23 wherein $R^8$ in formula I is the residue of an aliphatic acid having 1 to 8 carbon atoms, and $R^9$ in formula I is the residue of an aliphatic alcohol having 1 to 20 carbon atoms.

\* \* \* \* \*

UNITED STATES PATENT AND TRADEMARK OFFICE
CERTIFICATE OF CORRECTION

PATENT NO.    : 6,492,563 B2
DATED         : December 10, 2002
INVENTOR(S)   : Markus Gautschi, Caroline Plessis and Samuel Derrer It is certified that error appears in the above-identified patent and that said Letters Patent is hereby corrected as shown below:

Column 36,
Lines 31-35, 46-50 and 51-53, please rewrite claims 13, 16 and 17, to read as follows:
-- 13. A fragrance precursor according to claim 1 wherein in formula I $R^6$ and $R^7$ are H and $R^1$ to $R^5$ represent independently H, $-NO_2$, linear or branched $C_1$-$C_6$-alkyl, $C_1$-$C_6$-alkenyl, $C_1$-$C_6$-alkinyl or $C_1$-$C_4$ alkoxy. --

-- 16. A fragrance precursor according to claim 1 wherein the aliphatic or aromatic ring contains substituted or unsubstituted $C_1$-$C_4$-alkyl, $C_1$-$C_4$-alkenyl, or $C_1$-$C_4$-alkinyl residues. --

-- 17. A fragrance precursor according to claim 1 wherein the aliphatic or aromatic ring comprises one or more oxygen atoms. --

Column 37,
Lines 1-24, rewrite claims 19 as follows:
-- 19. A compound of formula I:

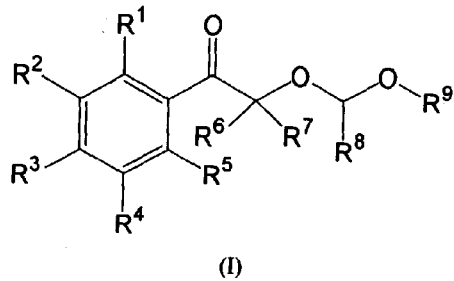

(I)

wherein,
$R^1$ to $R^5$ represent independently H, $-NO_2$, linear or branched $C_1$-$C_6$-alkyl, $C_1$-$C_6$-alkenyl, $C_1C_6$-alkinyl, or $C_1$-$C_4$-alkoxy,
$R^1$ and $R^2$, $R^2$ and $R^3$, $R^3$ and $R^4$, and $R^4$ and $R^5$ from together one or two aliphatic or aromatic rings,
$R^6$ and $R^7$ are independently H, lineat or branched $C_1$-$C_6$-alkyl, $C_1$-$C_6$-alkenyl, $C_1$-$C_6$-alkinyl, and
$R^8$ and $R^9$ are the residues of an acid and an alcohol respectively, which together form a fragrant ester. --

UNITED STATES PATENT AND TRADEMARK OFFICE
CERTIFICATE OF CORRECTION

PATENT NO. : 6,492,563 B2
DATED : December 10, 2002
INVENTOR(S) : Markus Gautschi, Caroline Plessis and Samuel Derrer It is certified that error appears in the above-identified patent and that said Letters Patent is hereby corrected as shown below:

<u>Column 37 cont'd, lines 36-46 through Column 38, lines 1-41,</u>
Rewrite Claim 23 as follows:

-- 23. A fragance presursor of formula I:

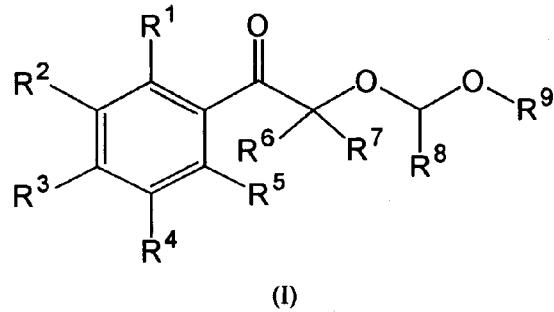

(I)

for a fragrant ketone of formula II:

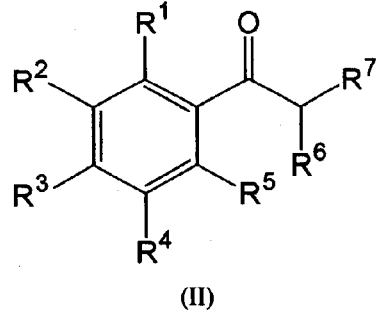

(II)

UNITED STATES PATENT AND TRADEMARK OFFICE
CERTIFICATE OF CORRECTION

PATENT NO. : 6,492,563 B2
DATED : December 10, 2002
INVENTOR(S) : Markus Gautschi, Caroline Plessis and Samuel Derrer It is certified that error appears in the above-identified patent and that said Letters Patent is hereby corrected as shown below:

and a fragrant ester of formula III:

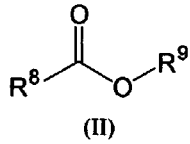

(II)

wherein, $R^1$ to $R^5$ represent independently H, $-NO_2$, linear or branched $C_1$-$C_6$-alkyl, $C_1$-$C_6$-alkenyl, $C_1$-$C_6$-alkinyl or $C_1$-$C_4$-alkoxy, $R^1$ and $R^2$, $R^2$ and $R^3$ and $R^3$ and $R^4$ and $R^4$ and $R^5$ may form together one or two aliphatic or aromatic rings, these rings may optionally contain linear or branched $C_1$-$C_4$-alkyl, $C_1$-$C_4$-alkenyl or $C_1$-$C_4$-alkinyl residues, and the above rings and residues may comprise one or more oxygen atoms, $R^6$ and $R^7$ are independently H, linear or branched $C_1$-$C_6$-alkyl-, $C_1$-$C_6$-alkenyl, $C_1$-$C_6$-alkinyl, and $R^6$ or $R^7$ may form with either $R^1$ or $R^5$ a carbocyclic ring optionally substituted by an aliphatic residue, $R^8$ in formula I is the residue of an aliphatic acid having 1 to 20 carbon atoms, and $R^9$ in formula I is the residue of an aliphatic alcohol having 1 to 20 carbon atoms. --

Signed and Sealed this

Twentieth Day of May, 2003

JAMES E. ROGAN
*Director of the United States Patent and Trademark Office*